United States Patent [19]

Aldwinckle

[11] Patent Number: 4,552,580

[45] Date of Patent: Nov. 12, 1985

[54] USE OF N-ACYL SARCOSINATE AND ITS SALTS AS COMPATIBILITY AGENTS FOR PESTICIDE/LIQUID FERTILIZER FORMULATIONS

[75] Inventor: Michael J. Aldwinckle, Stevenage, England

[73] Assignee: Ciba Geigy Corporation, Ardsley, N.Y.

[21] Appl. No.: 472,339

[22] Filed: Mar. 4, 1983

[30] Foreign Application Priority Data

Mar. 11, 1982 [GB] United Kingdom ............... 8207131

[51] Int. Cl.$^4$ ............................................. A01N 25/30
[52] U.S. Cl. ....................................... 71/3; 71/DIG. 1; 71/93; 71/120; 514/975
[58] Field of Search ............... 71/DIG. 1, 3; 514/975

[56] References Cited

U.S. PATENT DOCUMENTS 2,689,170  9/1954  King ...................................... 167/93
4,224,049  9/1980  Devisetty et al. ...................... 71/86

OTHER PUBLICATIONS

Moldovanyi et al., Chem. Abst., vol. 86 (1977) 60374k.

Primary Examiner—Catherine L. Mills
Attorney, Agent, or Firm—Edward McC. Roberts; Frederick H. Rabin

[57] ABSTRACT

A formulation for use as a compatibility agent in pesticide/liquid fertilizer formulations comprises:
(a) an N-acyl sarcosinate, or a salt thereof, having the formula:

$$RCON(CH_3)CH_2COOX \qquad (I)$$

wherein
R is a straight or branched chain alkyl or alkenyl residue having from 2 to 18 carbon atoms and X is hydrogen, an alkali metal, the ammonium radical, a primary, secondary or tertiary amine group or a hydroxyalkylamine group; and
(b) a solvent or mixture of solvents for component (a).

14 Claims, No Drawings

USE OF N-ACYL SARCOSINATE AND ITS SALTS AS COMPATIBILITY AGENTS FOR PESTICIDE/LIQUID FERTILIZER FORMULATIONS

The invention concerns the use of formulations in agriculture and particularly to the use of formulations as compatibility agents to improve the uniformity and stability of mixtures of liquid fertiliser and pesticides, thereby making it possible to spray previously unsprayable mixtures.

In general, pesticide and liquid fertiliser treatments need to be effected in separate stages because most pesticides are incompatible with liquid fertilisers, i.e. either they do not mix or they form unstable mixtures. This incompatibility can result in the formation of agglomerates of pesticide in the spray tank and thereby produce poor spraying performance with resultant damage to crops and/or ineffectiveness of treatment.

Clearly, there would be considerable economic advantages in combining the pesticide and liquid fertiliser treatments, as a result of eliminating one or more field operations.

Previous attempts to combine pesticides and liquid fertilisers into a single uniform and stable mixture have involved the incorporation of known emulsifying or suspending agents. The use of such materials, as compatibility agents, has proved unsatisfactory.

Surprisingly, we have now found that the use of certain N-acyl sarcosinates, or their salts, as compatibility agents, facilitates the production of uniform and stable suspensions or emulsions of pesticides in liquid fertilisers.

Accordingly, the present invention provides a method of using, as a compatibility agent in pesticide/liquid fertilisers mixtures, a formulation comprising:

(a) N-acyl sarcosinate or a salt thereof having the formula:

RCON(CH$_3$)CH$_2$COOX    (I)

wherein R is a straight or branched chain alkyl or alkenyl residue having from 2 to 18 preferably 8–17 carbon atoms and X is hydrogen, an alkali metal, the ammonium radical, a primary, secondary or tertiary amine group or a hydroxyalkylamine group; and (b) a solvent or mixture of solvents for the component a).

Preferably, the compatibility agent formulations used in the present invention contain 20–99, more preferably 60–80% by weight of solvent and 1–80 more preferably 20–40% by weight of the compound of formula I.

In the compounds of formula I, alkyl substituents R include ethyl, propyl, butyl, pentyl, hexyl, heptyl, nonyl, undecanyl, tridecanyl, pentadecanyl and heptadecanyl groups and alkenyl substituents R include prop-2-enyl, but-3-enyl, pent-4-enyl, hex-5-enyl, hept-6-enyl and heptadec-8-enyl groups.

Examples of compounds of formula I include ethanoyl-, propanoyl-, butanoyl-, hexanoyl-, octanoyl-, decanoyl-, lauroyl-, tetradecanoyl-, hexadecanoyl- and octadecanoyl-sarcosines, and in particular their salts e.g. their alkali metal especially their sodium salts; their ammonium salts; their alkyl (1–4) amine salts; and their triethanolamine salts.

Of particular interest are salts of compounds of formula I in which R is 8–17 C alkyl, most especially N-lauroyl sarcosinate sodium salt having the formula:

CH$_3$(CH$_2$)$_{10}$CON(CH$_3$)CH$_2$COONa

The solvent, component (b), may be e.g. an aqueous system (which may or may not contain one or more co-solvents) or a non-aqueous system e.g. a polar alcohol. Examples of solvent components are water (which is the preferred solvent); methanol, methanol/water mixtures (in all proportions); ethanol-water mixtures containing up to 50% by weight of ethanol; propan-2-ol/water mixtures containing up to 50% by weight of propan-2-ol; and methanol/ethanol mixtures containing up to 50% by weight of ethanol.

The most preferred compatibility agent used in the invention is an aqueous solution of sodium lauroyl sarcosinate containing approximately 30% by weight of N-lauroyl sarcosinate sodium salt. This preferred material is commercially available as a colourless solution having a specific gravity of approximately 1.035 g/ml and a viscosity of 20 cps.

The present invention also provides a stable and uniform combined liquid fertiliser/pesticide mixture comprising:

(i) liquid fertiliser;
(ii) pesticide;
(iii) a sarcosinate of formula I as hereinbefore defined; and
(iv) a solvent or mixture of solvents for component (iii); as well as methods of producing such mixtures.

The concentrations of the liquid fertiliser and the pesticide components of the combined mixtures of the invention will vary according to the nature of the particular active ingredient and its use rate.

The concentration of the sarcosinate compound of formula I is preferably within the range of from 0.01 to 5%, more preferably from 0.01 to 1% by volume, based on the total volume of the mixture.

The preferred method of producing the combined fertiliser/pesticide mixtures of the invention comprises:

(a) adding to the liquid fertiliser, e.g. in the spray tank, from 0.01 to 5%, preferably from 0.01 to 1% by volume (based on the total volume of the mixture) of a solution of the sarcosinate compound of formula I and optionally mixing thoroughly;

(b) adding the pesticide to the mixture so produced; and then (c) thoroughly agitating the whole mixture.

As an alternative procedure, a premix of the required amounts of pesticide and a solution of the compound of formula I may be prepared in water; this premix added to the required amount of liquid fertiliser present e.g. in the spray tank, and the whole is then mixed thoroughly. This premix variation is recommended for those instances in which fertilisers of high phosphate content and high viscosity are used.

The liquid fertilisers used in the mixtures of the present invention may be e.g. liquid nitrogen fertilisers (optionally containing phosphate and/or potash components) and foliar feeds or other formulations containing micronutrients e.g. trace elements. Such mixed liquid fertilisers are usually designated by their percentage weight of nitrogen, phosphorus and potassium (N-P-K) ratios e.g. 4-10-10, 6-18-18 or 10-30-0.

Fertilisers not containing nitrogen (e.g. 0-6-6) may also be used. Pesticides which present particular problems in terms of their incompatibility with liquid fertilisers include a 50% w/v terbutryne suspension concentrate, a 50% w/v isoproturon suspension concentrate, a 50% w/v atrazine suspension concentrate, a 50% w/v chlortoluron suspension concentrate, a 10% w/w metalaxyl+48% w/w mancozeb wettable powder, a 35% w/v terbutryne+15% w/v terbuthylazine suspension concentrate and a 24% w/w chlorfenvinphos emulsifiable concentrate.

As already mentioned, variations in such parameters as density, viscosity, salt concentration and nutrient analysis of liquid fertilisers, and the different effects on such parameters when various pesticides are added, can affect the compatibility balance between the fertiliser and the pesticide. Moreover, a liquid fertiliser with a nominally identical composition may be formulated sufficiently differently by various manufacturers that the fertiliser may respond variably in terms of its compatibility with the pesticide component.

For these reasons, and in order to determine the optimum amount of compatibility agent required for particular liquid fertiliser/pesticide combinations, it is desirable to carry out a compatibility test on each individual fertiliser/pesticide combination.

A suitable laboratory compatibility test procedure is as follows:

Compatibility Test Procedure

1. To 2×100 ml measuring cylinders add the appropriate dose of fertiliser. Mark one cylinder with a "+" sign.
2. Add 0.05 ml of compatibility agent to the marked cylinder, stopper the cylinder and invert 10 times.
3. Add the required amount of pesticide to both cylinders. If the pesticide is a wettable powder formulation, a pre-slurry will need to be made using liquid fertiliser from the appropriate cylinder.
4. Stopper the cylinders and invert 10 times.
5. Leave the cylinders to stand and inspect the uniformity of the suspensions at 5 minute intervals up to 30 minutes.

Evaluation of Results

If the mixture in the marked cylinder does not show a significant improvement in stability and uniformity when compared to the mixture in the unmarked cylinder, the test is repeated using 0.1 ml or more of the compatibility agent. If a level of 0.5 ml is reached and the mixture is still not sufficiently stable and uniform, a premix of pesticide with compatibility agent with an equal amount of water is prepared and added to the liquid fertiliser with mixing to yield the optimum result.

When evaluating compatibility to determine the appropriate use rate of the compatibility agent, a minimum stability period of 30 minutes without agitation is considered the acceptable criterion. Any mixture which requires the use of a compatibility agent should be sprayed as soon after mixing as possible with minimum time taken for transportation between fields.

The suspensions and emulsions of liquid fertiliser and pesticide combinations produced according to the invention are more uniform in composition and more stable than those produced without the addition of sarcosinate compounds of formula I.

The invention is further illustrated by the following Examples.

EXAMPLE 1

The compatibility test procedure was used to evaluate the compatibility of a herbicidal 50% w/v terbutryne suspension concentrate (use rate 5.6 liters per ha) with a 2.3-10-10 liquid fertiliser (use rate 354 liters per ha), a 4-12-12 liquid fertiliser (use rate 400 liters per ha), a 4-10-10 liquid fertiliser (use rate 330 liters per ha) and a 3.3-10-10 liquid fertiliser (use rate 280 liters per ha). The compatibility agents used were based on (a) oleoyl sarcosinate acid form; (b) oleoyl sarcosinate, sodium salt;

(c) oleoyl sarcosinate, ammonium salt and (d) oleoyl sarcosinate, triethanolamine salt. Each sarcosinate was dissolved in water at a concentration of 30% w/w and the resultant compatibility agents were used at a rate of 0.05%, equivalent to 50 ml per 100 liters of liquid fertiliser. Controls containing no compatibility agent were also prepared.

In the control cylinders, the pesticide particles began to flocculate immediately and separation was complete within 5 minutes. In the cylinder containing the oleoyl sarcosinate acid form, flocculation began after 5 minutes and separation was complete after 15 minutes. In the cylinders containing the other compatibility agents, stability and uniformity remained for over 6 hours.

EXAMPLE 2

The compatibility test procedure was used to evaluate the compatibility of the herbicidal 50% w/v isoproturon suspension concentrate (use rate 5 liters per hectare) with a 3-10-6 liquid fertiliser (use rate 500 liters per hectare). The compatibility agents used were based on:

(a) lauroyl sarcosinate sodium salt
(b) coconut oil sarcosinate sodium salt
(c) palm kernel oil sarcosinate sodium salt and
(d) oleoyl sarcosinate sodium salt.

The sarcosinates were separately dissolved in water at a concentration of 30% w/w and the resultant compatibility agents were used at a rate of 0.05%, equivalent to 50 ml to 100 liters of liquid fertiliser. A control cylinder with no compatibility agent was also prepared.

In the control, dispersion was not complete and flocculation of the dispersed herbicide particles were observed immediately. Separation was complete within 5 minutes.

In the cylinder containing the oleoyl sarcosinate sodium salt flocculation began after 5 minutes and separation was complete after 10 minutes.

In the cylinder containing the palm kernel oil sarcosinate sodium salt flocculation began after 5 minutes and separation was complete after 15 minutes.

In the cylinder containing the coconut oil sarcosinate sodium salt, flocculation began after 5 minutes and separation was complete after 20 minutes.

In the cylinder containing the lauroyl sarcosinate sodium salt, flocculation began after 15 minutes and separation was complete after 40 minutes.

EXAMPLE 3

The compatibility test procedure, described hereinbefore, was used to evalate the compatibility of a wettable powder funcicide containing metalaxyl 10%+mancozeb 48% (use rate 3 kg per ha), with the following foliar feeds; Complessal ® (use rate 4.2 kg per ha), Stimufol ® (use rate 2 kg per ha) and Polyverdol ®

(use rate 8 kg per ha), all of which are formulations containing micronutrients.

The compatibility agent used was a formulation containing 32.5% of a coconut oil sarcosinate (sodium salt) and 67.5% water. The foliar feeds were first dispersed in water at a rate equivalent to 200 liters of solution per ha and the compatibility agent was added at a rate equivalent to 300 ml per 100 liters of solution (0.3%). The 10% metalaxyl+48% mancozeb fungicide was then added to the foliar feed solutions. Controls containing no compatibility agent were also prepared.

In the controls, complete separation of the fungicide from the foliar feed solution occurred in less than 5 minutes. In the measuring cylinders containing compatibility agent, excellent suspensions were formed. After 30 minutes further observation were made and the suspensions in the measuring cylinders containing the compatibility agent remained uniform with no evidence of separation.

EXAMPLE 4

The compatibility test procedure was used to evaluate the compatibility of a herbicidal 50% w/v chlortoluron suspension concentrate (use rate 7 liters per ha) with 2-6-12 or 4-10-10 or 6-13-8 clear liquid fertilisers (use rate 300 liters per ha).

The premix method was used with compatibility agent at the rate of 0.3% (300 ml per 100 liters of fertiliser). The compatibility agent used was a palm kernel oil sarcosinate sodium salt 30% w/v in water. Control cylinders with no compatibility agent were also prepared.

In the controls, separation was complete within 5 minutes. The cylinders containing compatibility agent remained stable after 30 minutes.

EXAMPLE 5

The compatibility test procedure was used to evaluate the compatibility of a insecticidal 25% w/v chlorofenvinphos emulsifiable concentrate (use rate 5.6 liters per ha) with a 3.3-10-10 clear liquid fertiliser (use rate 280 liters per ha).

The compatibility agent used was 30% by weight lauroyl sarcosinate sodium salt and 70% methanol.

The premix method was used with compatibility agent at a rate of 0.3% by volume (300 ml per 100 liters of fertilisers). A control cylinder containing no compatibility agent was also prepared.

In the control cylinder, separation was complete within 5 minutes, whereas in the cylinder containing the compatibility agent, the mixture remained uniform for 30 minutes.

EXAMPLE 6

The compatibility test procedure was used to evaluate a mixture of a 50% w/v atrazine suspension concentrate (use rate 3.4 liters per hectare) and a 6-13-8 liquid fertiliser (use rate 200 liters per hectare). The 50% atrazine suspension concentrate was premixed with an equal volume of water, to ensure complete dispersion in the fertiliser, and to this was added a 30% w/v aqueous solution of N-lauroyl sarconsinate sodium salt at a rate equivalent to 300 ml of compatibility agent per 100 liters of fertiliser. This mixture was then added to the fertiliser.

A control containing no compatibility agent was prepared using the same method.

In the control cylinder, flocculation was apparent after 5 minutes and separation was complete after 30 minutes.

In the cylinder containing the compatibility agent flocculation was not apparent until after 25 minutes and separation was not complete until well over 120 minutes had elapsed.

What is claimed is:

1. A combined liquid fertiliser/pesticide mixture comprising
(i) a liquid fertiliser;
(ii) a pesticide;
(iii) a compound of the formula $$RCON(CH_3)CH_2COOX$$

wherein
R is $C_8$–$C_{17}$ alkyl or alkenyl, and
X is hydrogen, and alkali metal, ammonium, $C_1$–$C_4$ alkylamine or triethanolamine; and
(iv) a solvent or mixture of solvents for (iii).

2. A mixture according to claim 1 wherein the concentration of the compound is within the range of from 0.01 to 5% by volume, based on the total volume of the mixture.

3. A mixture according to claim 2 wherein the concentration of the compound is within the range of from 0.01 to 1% by volume, based on the total volume of the mixture.

4. A mixture according to claim 1 wherein the liquid fertiliser is a liquid nitrogen fertiliser or a foliar feed.

5. A mixture according to claim 1 wherein the pesticide is a terbutryne suspension concentrate, an isoproturon suspension concentrate, an atrazine suspension concentrate, a chlortoluron suspension concentrate, a metalaxyl/mancozeb wettable powder, a terbutryne/terbuthylazine suspension concentrate or a chlorfenvinphos emulsifiable concentrate.

6. A mixture according to claim 1 wherein the solvent is water.

7. A process for combining pesticides and liquid fertilisers into a single uniform and stable mixture which comprises admixing the pesticide and fertiliser with (a) an N-acyl sarcosinate or a salt thereof having the formula $$RCON(CH_3)CH_2COOX$$

wherein
R is $C_8$–$C_{17}$ alkyl or alkenyl, and
X is hydrogen, and alkali metal, ammonium, $C_1$–$C_4$ alkylamine or triethanolamine,
and (b) a solvent or mixture of solvents for (a).

8. A process according to claim 7 in which (a) is used in the form of a salt.

9. A process according to claim 7 in which the admixture contains from 20 to 99% by weight of solvent (b) and from 1 to 80% by weight of the compound (a).

10. A process according to claim 9 containing from 60 to 80% of solvent (b) and from 20 to 40% of the compound (a).

11. A process according to claim 10 wherein the compound (a) is a $C_9$–$C_{18}$ acyl sarcosinate or its sodium, ammonium or triethanolamine salt.

12. A process according to claim 11 in which compound (a) is sodium N-lauroyl sarcosinate.

13. A process according to claim 12 in which the formulation is an aqueous solution containing about 30% by weight of sodium N-lauroyl sarcosinate.

14. A mixture according to claim 4 wherin the liquid fertiliser is a liquid nitrogen fertiliser containing phosphate and/or postash components.

* * * * *